United States Patent [19]
Adams

[11] Patent Number: 5,156,595
[45] Date of Patent: Oct. 20, 1992

[54] DILATATION BALLOON CATHETER AND METHOD OF MANUFACTURING

[75] Inventor: Daniel O. Adams, Blaine, Minn.

[73] Assignee: Scimed Life Systems, Inc., Maple Grove, Minn.

[21] Appl. No.: 814,246

[22] Filed: Dec. 23, 1991

Related U.S. Application Data

[63] Continuation of Ser. No. 458,327, Dec. 28, 1989, abandoned.

[51] Int. Cl.⁵ .............................................. A61M 29/00
[52] U.S. Cl. ...................................... 604/96; 604/102
[58] Field of Search ................. 604/93, 96, 101, 102; 606/191, 194

[56] References Cited

U.S. PATENT DOCUMENTS

| | | | |
|---|---|---|---|
| 3,435,826 | 4/1969 | Fogarty | 606/194 |
| 3,485,234 | 12/1969 | Stevens | 128/657 |
| 3,889,685 | 6/1975 | Miller, Jr. et al. | 128/348 |
| 4,137,906 | 2/1979 | Akiyama et al. | 128/2 A |
| 4,413,989 | 11/1983 | Schjeldahl et al. | 604/96 |
| 4,646,742 | 3/1987 | Packard et al. | 128/344 |
| 4,665,925 | 5/1987 | Millar | 128/663 |
| 4,811,737 | 3/1989 | Rydell | 128/344 |
| 4,820,349 | 4/1989 | Saab | 128/344 |
| 4,838,268 | 6/1989 | Keith et al. | 128/344 |
| 4,846,174 | 7/1989 | Willard et al. | |
| 4,877,031 | 10/1989 | Conway et al. | |
| 4,884,579 | 12/1989 | Engelson | 128/657 |
| 4,917,088 | 4/1990 | Crittenden | 604/96 |
| 4,921,478 | 5/1990 | Solano et al. | |
| 4,940,062 | 7/1990 | Hampton et al. | |
| 4,943,278 | 7/1990 | Euteneuer et al. | 604/96 |
| 4,976,720 | 12/1990 | Machold et al. | |
| 4,998,917 | 3/1991 | Gaiser et al. | |
| 4,998,923 | 3/1991 | Samson et al. | |
| 5,032,113 | 7/1991 | Burns | |
| 5,034,001 | 7/1991 | Garrison et al. | |
| 5,035,705 | 7/1991 | Burns | |
| 5,042,985 | 8/1991 | Elliott et al. | |
| 5,047,045 | 9/1991 | Arney et al. | |

*Primary Examiner*—Robert Bahr
*Assistant Examiner*—Linda C. M. Dvorak
*Attorney, Agent, or Firm*—Kinney & Lange

[57] ABSTRACT

An angioplasty catheter has a one-piece, flexible elongated tube in which a hollow proximal section tapers to form a solid distal core with a solid cross-section. The core further tapers to form a safety wire at the distal end of the catheter. An inflatable balloon circumscribes the elongated tube and the interior of the balloon is in fluid communication with a lumen defined by the hollow proximal section of the tube through at least one aperture extending through the tube wall and into the balloon interior. A coil spring extends distally from the balloon about the solid distal core and safety wire, with the safety wire secured to an end cap of the coil spring.

49 Claims, 3 Drawing Sheets

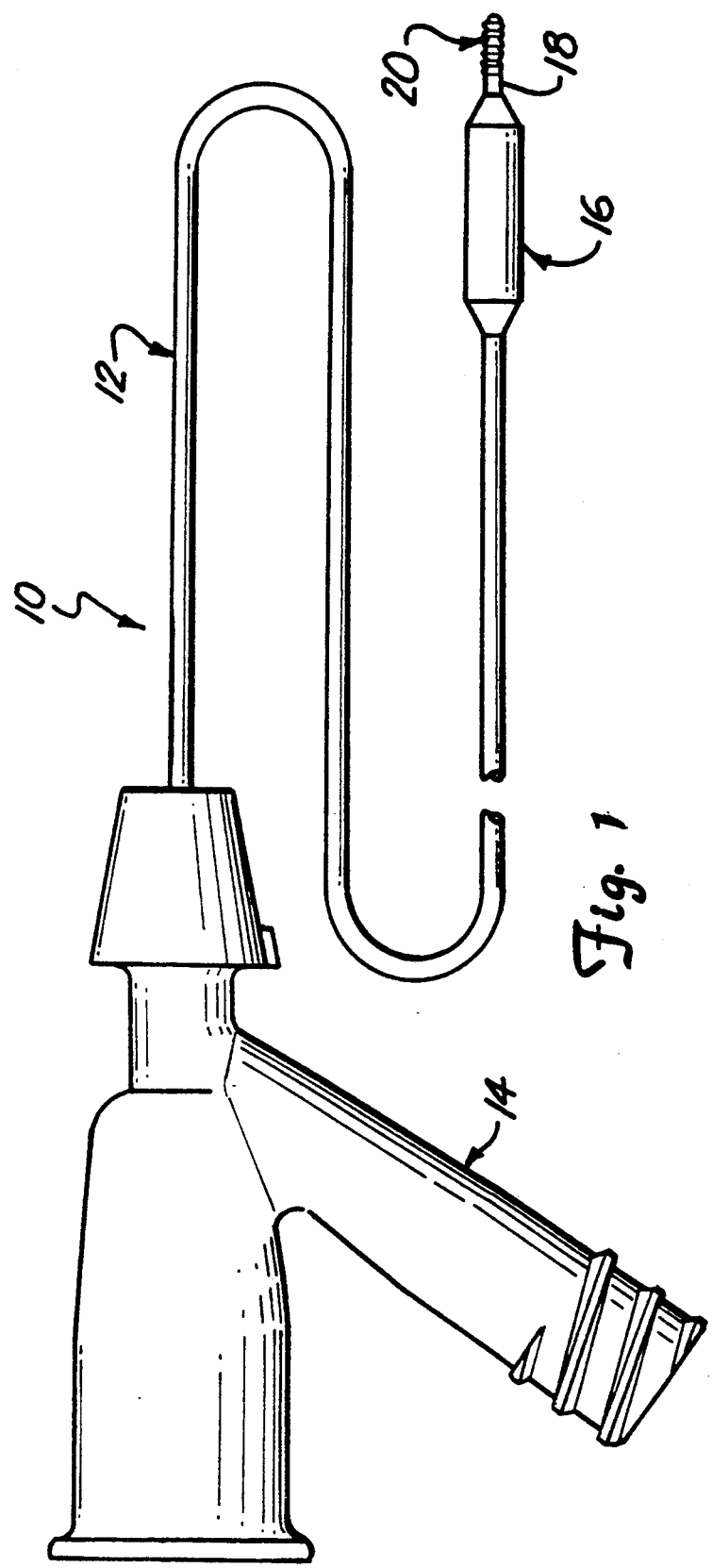

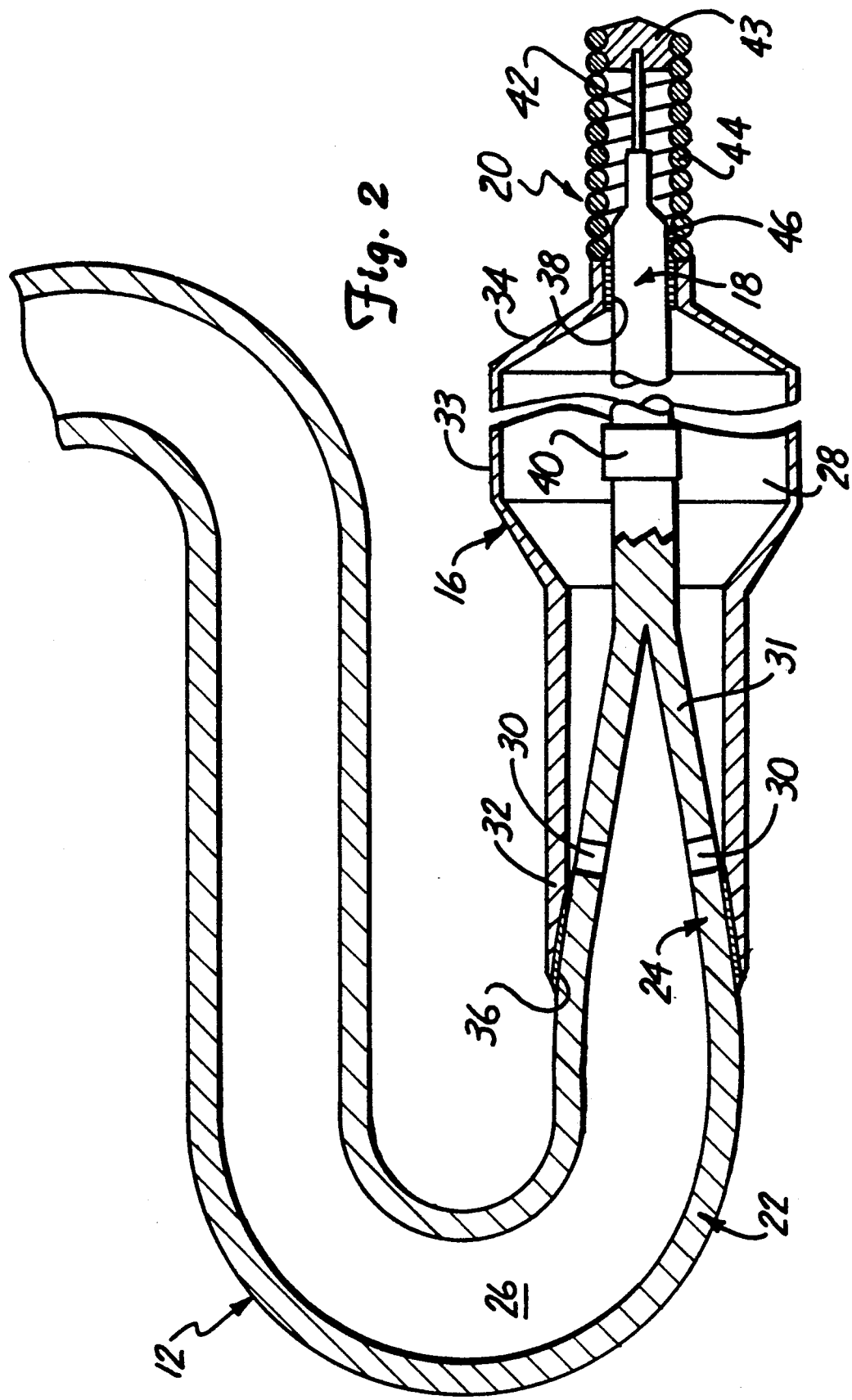

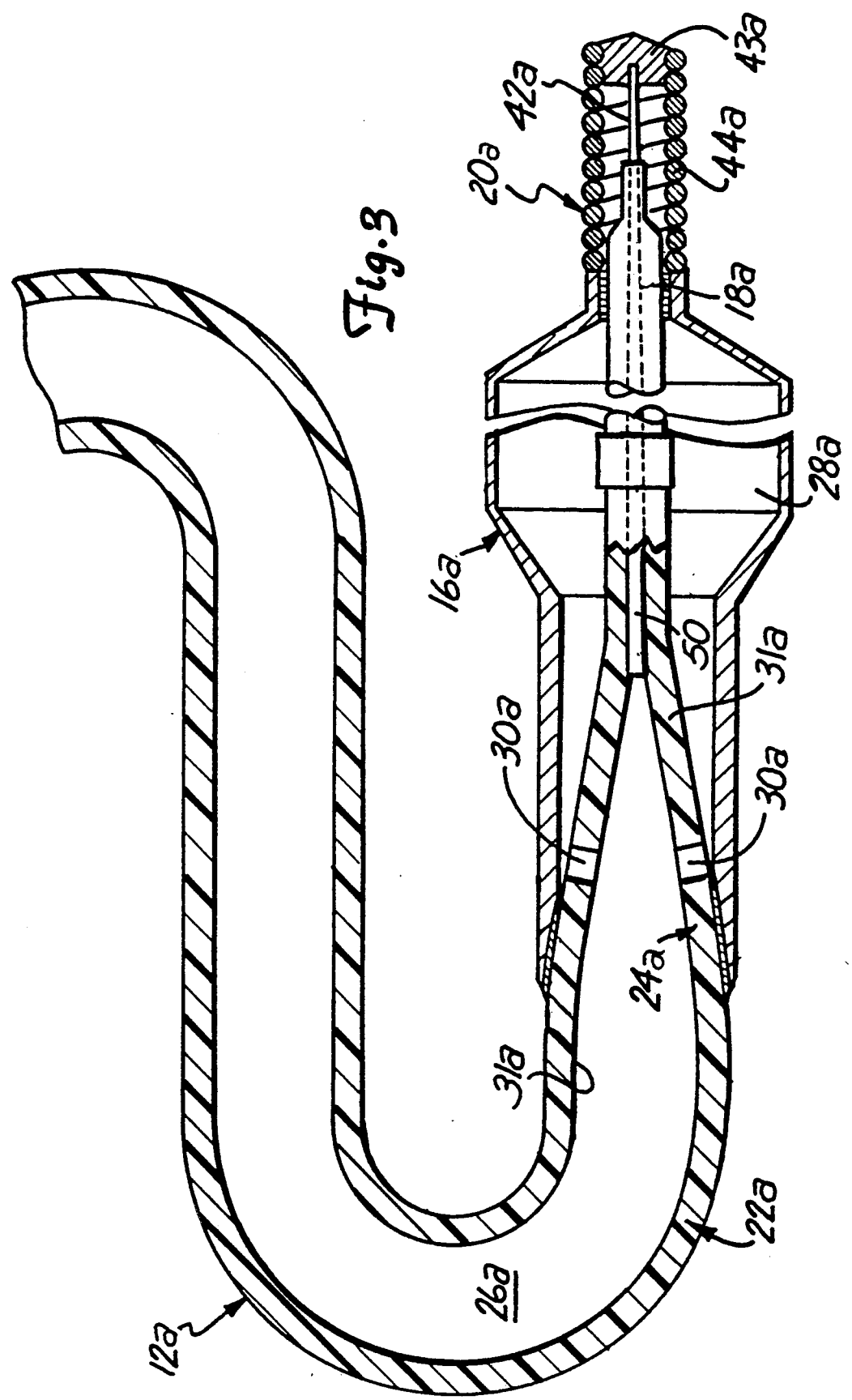

DILATATION BALLOON CATHETER AND METHOD OF MANUFACTURING

This is a continuation of application Ser. No. 07/458,327 filed on Dec. 28, 1989, abandoned as of the date of this application.

BACKGROUND OF THE INVENTION

1. Field of the Invention.

The present invention relates to the field of angioplasty. In particular, the present invention relates to a dilatation balloon catheter.

2. Description of the Prior Art.

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying fluid under pressure through an inflation lumen to the balloon. The inflation of the balloon causes stretching of the artery and pressing of the lesion into the artery wall to re-establish acceptable blood flow through the artery.

Two commonly used types of dilatation catheters are referred to as "over-the-wire" and "non-over-the-wire" catheters. An over-the-wire catheter is one in which a separate guide wire lumen is provided so that a guide wire can be used to establish a path across the stenosis. The dilatation catheter can then be advanced over the guide wire until the balloon is positioned across the stenosis. A non-over-the-wire catheter acts as its own guide wire, and thus there is no need for a separate guide wire lumen. A non-over-the-wire catheter can therefore achieve a smaller outer diameter for its main shaft since a guide wire lumen is not required.

There has been a continuing effort to reduce the profile and shaft size of the dilatation catheter to allow the catheter to not only reach, but also cross, a very tight stenosis. A successful dilatation catheter must also be sufficiently flexible to pass through tight curvatures, especially in the tortuous coronary arteries. A further requirement of a successful dilatation catheter is its "pushability." This involves the transmission of longitudinal forces along the catheter from its proximal end to its distal end allowing a physician to push the catheter through the vascular system and across the stenosis.

SUMMARY OF THE INVENTION

The present invention is a non-over-the-wire dilatation catheter which has a low profile shaft, is flexible, has good torque response and pushability, and which also is relatively simple to manufacture.

One embodiment of the inventive catheter includes a one-piece, flexible elongate tube having a hollow proximal end formed by a tubular wall which defines a lumen, and having a distal end. The distal end of the tube has a tapered section, which has a diameter which necks down from a first diameter of the tube to a second diameter smaller than the first diameter. At a distal end of the tapered section, the lumen terminates and a generally solid distal core is formed distally of the tapered section. An inflatable balloon segment circumscribes the tube and has a proximal end bonded to the tube adjacent the tapered section and a distal end bonded to the tube adjacent the solid section thereof. The interior of the balloon segment is in communication with the lumen via at least one aperture extending through the tubular wall.

Preferably, a flexible coil spring tip extends distally from the tube and balloon segment. The distal end of the tube tapers to form a safety wire extending within the coil spring and is attached to an end cap of the coil spring. In a preferred embodiment, the tube is formed from a stainless steel hypotube and coated with a lubricious material in the proximal unnecked segment.

In another embodiment, the tube is formed from semi-rigid plastic tubing. In the distal end, the tube has a tapered section which tapers from a first diameter to a distal section of a smaller second diameter, formed about a metal core wire. The distal section has a generally solid cross-section. The metal core wire tapers and extends out of the distal section to define a safety wire, which extends within a coil spring, and attaches to an end cap of the coil spring.

The inventive catheter is relatively simple to manufacture by a method including the formation of a lumen from an elongated tube having a proximal section and a distal section; the formation of a tapered portion in the distal section of the tube wherein the cross-sectional diameter of the tube tapers distally to terminate the lumen and form a generally solid distal core, either of metal or plastic, of plastic formed about a metal core wire; and mounting an inflatable balloon on the distal section of the tube, with a proximal end of the balloon segment secured to the tube proximally of the aperture and a distal end of the balloon segment secured to the solid distal core.

Preferably, the cross-sectional diameter of the distal core wire is further reduced to define a distal safety wire segment of the tube. In the case where the tube is semi-rigid plastic tubing, the metal core wire is reduced in cross-sectional diameter to form a safety wire segment of the metal core wire. A coil spring is secured to the distal core wire to extend distally from the balloon about the distal safety wire segment. The distal end of the distal safety wire segment is then secured to a distal end cap on the coil spring.

BRIEF DESCRIPTION OF THE INVENTION

FIG. 1 shows generally an angioplasty balloon catheter in accordance with the present invention.

FIG. 2 is a detailed sectional view of the distal portion of a first preferred embodiment the angioplasty catheter.

FIG. 3 is a detailed sectional view of the distal portion of a second preferred embodiment of the angioplasty catheter.

DETAILED DESCRIPTION OF THE PREFERRED EMBODIMENTS

FIG. 1 shows generally an angioplasty balloon catheter 10 in accordance with the present invention, including a catheter tube 12, inflation manifold 14, and an inflatable balloon 16. A distal section 18 of the catheter 10 has a flexible spring tip 20. Catheter tube 12 is an elongated, flexible, one-piece tube, preferably of stainless steel, or of semi-rigid plastic, coated on its outer surface with a lubricious material, such as silicon or Teflon. The lubricious coating allows the catheter to move with ease through the vasculature of the body. Inflation manifold 14 is attached at the proximal end of the tube 12 to provide fluid under pressure to inflate the balloon segment 16. Inflatable balloon 16 is preferably fabricated from a polymeric material such as polyolefin copolymer.

In one preferred embodiment, angioplasty balloon catheter 10 has a length of approximately 135 centimeters with catheter tube 12 having an outer diameter between 0.020 and 0.040 inch in its proximal end and with the coil spring tip 20 at the distal end of catheter 10 having an outer diameter between 0.012 to 0.016 inch.

FIG. 2 shows in detailed sectional view the balloon or distal portion of a first preferred embodiment of the angioplasty balloon catheter 10 of the present invention. In this embodiment, catheter tube 12 is a stainless steel hypotube and has a hollow proximal section 22, of a first diameter, which tapers at elongated tapered section 24 to terminate an inflation lumen 26 and form distal section 18 which has a second diameter that is smaller than the first diameter. The tapered section 24 of the tube 12 tapers from a tube (hollow proximal section 22) to elongated distal section 18, which has a generally solid cross-section, as seen in FIG. 2. In a preferred embodiment, the tapering is uniform in tube diameter reduction, but a stepped or progressive reduction will also work. An inflation lumen 26 is defined within the hollow proximal section 22 of the tube 12. The lumen 26 extends into the elongated tapered section 24 of the tube 12, and is in fluid communication with an interior 28 of the balloon 16 via one or more apertures extending through the tube, as at apertures 30 through tube wall 31 of the tapered section 24, as seen in FIG. 2.

The balloon 16 has a proximal section 32, an inflatable section 33, and a distal section 34. The proximal section 32 of the balloon 16 is connected to the tapered section 24 at proximal adhesive joint 36, and the distal section 34 of the balloon 16 is connected to the solid distal section 18 at a distal adhesive joint 38. The balloon ends are preferably attached to their respective tube sections by an adhesive such as epoxy. At least one radiopaque marker band 40 circumscribes the generally solid distal section 18 of the tube within balloon 16. The proximal section 32 of the balloon segment 16 may be formed from a separate flexible plastic tube, such as polyethylene for increased flexibility, having its proximal end bonded to the proximal tube section 22 (proximally of apertures 30) and its distal end bonded to the proximal end of balloon segment 33.

Preferably, elongated solid distal section 18 of tube 12 further tapers distally to form safety wire 42. Safety wire 42 is attached by braze 43 at a distal end of a coil spring 44 to form coil spring tip 20. Flexible coil spring tip 20 serves to safely guide catheter 10 through the tortuous passages of the coronary arteries. Coil spring 44 is mounted on solid section 18 at braze or solder joint 46 adjacent distal adhesive joint 38. The coil spring tip 20 is bendable, and the safety wire 42 can be bent to a position and will retain the bend, thus facilitating the steerability of the catheter 10 through a patient's vascular system. In use, torque is applied to a proximal end of tube 12, and is transmitted by (through) tube 12, tapered section 24, distal section 18 to spring tip 20.

FIG. 3 shows a second preferred embodiment of the angioplasty balloon catheter of the present invention. In this embodiment, a catheter tube 12a has a hollow proximal section 22a, of a first diameter, which tapers distally at elongated tapered section 24a to a second smaller diameter. An elongated distal section 18a defines in part, the reduced diameter portion of tube 12a. In this embodiment, catheter tube 12a is semi-rigid plastic tubing, and distal section 18a of the semi-rigid plastic tube is formed about a central metal core wire 50. Together, the plastic tubing and metal core wire 50 comprise distal section 18a, which is essentially solid in lateral cross-section. Balloon 16a is identical to balloon 16 described with reference to the embodiment of FIG. 2.

An inflation lumen 26a is defined within the hollow proximal section 22a of the tube 12a. The lumen 26a extends into the elongated tapered section 24a of the tube 12a and is terminated at a point where the tube 12a fits about the metal core wire 50 at distal section 18a. The lumen 26a is in fluid communication with an interior 28a of the balloon 16a via one or more apertures extending through the tube, as at apertures 30a through tube wall 31a of the tapered section 24a, as seen in FIG. 3.

Preferably, metal core wire 50 is reduced in diameter as it extends distally and out of the distal section 18a to form safety wire 42a. Safety wire 42a is attached by braze 43a at distal end of a coil spring 44a to form coil spring tip 20a. Again, flexible (and bendable) coil spring tip 20a serves to safely guide the catheter of the present invention through the tortuous passages of the coronary arteries.

The angioplasty balloon catheter of the present invention is relatively simple to manufacture. The method of manufacturing catheter includes the following steps. A lumen is formed from an elongated tube having a proximal section and a distal section. The tube can be either metal or semi-rigid plastic tubing. A tapered portion is formed in the distal section of the tube. In the tapered section, the cross-sectional diameter of the tube is decreased distally. Preferably, the tapered section tapers uniformly from a first diameter to a smaller second diameter. In the instance where the tube is metal, a distal portion of the reduced cross-sectional diameter of tube forms an elongated, generally solid, distal core, as seen in FIG. 2. Thus, a single-piece metal inflation lumen and balloon core is created by a metal tube that is reduced distally to a solid core or wire. In the instance where the tube is plastic, the cross-sectional diameter of the tube is also decreased distally in the tapered section and the tube tapers to a solid distal core section, or in a preferred embodiment, the tube tapers uniformly to a distal section where the plastic tube is formed about a metal core wire as seen in FIG. 3. Thus, an inflation lumen and balloon core are created by a semi-rigid plastic tube which is reduced distally to fit about a metal core wire.

In either arrangement, at least one aperture through the tapered section is then provided, and an inflatable balloon segment is mounted on the distal section of the tube. The proximal end of balloon segment is secured to the tube proximally of the aperture, and a distal end of balloon segment is secured to the solid core. As mentioned above, a separate proximal or waist segment of the balloon (extending generally over the tapered section of the tube) may be provided. This allows this proximal waist (i.e., segment 32 in FIG. 2) to be formed from a material different from the balloon segment, and which has enhanced flexibility characteristics, thereby achieving improved trackability.

The tapered section of the tube can be formed by any suitable means such as rolling or compressive loading of the tube. In this formation process, heating and axial stretching of the tube may be performed as well. The distal reduction in diameter of the tube thus increases flexibility of the tube in its distal environs, which necessarily must be the most flexible portion of the catheter to permit its advancement through the convoluted coronary arteries. Grinding techniques may also be employed in combination with the manufacturing processes mentioned above to achieve the reduced diameter tube and to also achieve reduced wall thicknesses for those distal worked portions of the tube (the tapered section 24 and distal section 18, as seen in FIG. 2).

Preferably, the generally solid distal core is further formed to reduce its cross-sectional diameter to a very small wire or ribbon core, thus defining a bendable distal safety wire segment 42 of the tube 12, in the case where tube 12 is metal (see FIG. 2). In the case where the tube 12 is semi-rigid plastic tubing, the metal core wire 50 is further formed to reduce its cross-sectional diameter to a very small wire or core, thus defining a distal safety wire segment 42a of the metal core wire 50 (see FIG. 3). A coil spring is then secured to the solid distal section of the tube to extend distally from the balloon about the distal safety wire segment. A distal end of the distal safety wire segment is secured to the coil spring, thus defining a distal tip on the catheter which is flexible and has no sharp edges. This minimizes the possibility of inadvertently puncturing or scraping the walls of the artery as the catheter is moved therethrough.

In use, a physician first follows the typical angioplasty procedure of positioning a guide catheter in the vascular system. The angioplasty balloon catheter of the present invention is then advanced distally through the guide catheter and into the stenosed coronary artery. The physician then further pushes the catheter to the point at which the inflatable balloon thereon is positioned across the stenosis. By using a dye injected into the coronary artery through the guide catheter which is detectable by fluoroscopy, the stenosis position is detectable. The radiopaque marker on the catheter also is detectable by fluoroscopy, thereby permitting the physician to accurately position the balloon across the stenosis for inflation. The flexible and steerable distal coil spring tip of the catheter aids in the safe and effective movement of the catheter through the tortuous passages of the coronary artery. Using an inflation device (not shown) coupled to the inflation manifold 14, the physician inflates the balloon with an inflation medium (typically a 50/50 solution of saline and Renografin 76) through lumen 26 and apertures 30 of tube 12 (FIG. 2). The inflatable section 33 of the balloon 16 expands and stretches the arterial wall, pressing the lesion into the arterial wall and re-establishing acceptable blood flow through the artery. The balloon 16 is then deflated via negative pressure applied from the inflation manifold 14. The artery is again visualized using dye and angiography, and if the stenosis has been dilated, the catheter is removed. If the stenosis has not been sufficiently dilated, the inflation procedure may be repeated.

In conclusion, the present invention is an improved angioplasty dilatation catheter. The one-piece design for the proximal inflation tube and distal balloon core and catheter tip allows for good torque transmission from the proximal to distal ends and is relatively easy to manufacture. The design wherein a semi-rigid plastic tube is formed about a distal metal core wire also allows for good torque transmission from the proximal to distal ends and is relatively easy to manufacture. In the case where the catheter tube is metal, the inventive catheter does not require a separate guide wire or safety wire since the one-piece tube itself tapers distally to form the guide or safety wire. In the case where catheter tube is semi-rigid plastic, the guide/safety wire is provided by the metal core wire onto which the plastic tube is formed. These constructions provide a small outer diameter for the catheter, thus lessening the friction problems inherent in advancing an elongated tube longitudinally, and also allowing less obstruction in the guide catheter and coronary artery to the flow of dye.

Although the present invention has been described with reference to preferred embodiments, workers skilled in the art will recognize that changes may be made in form and detail without departing from the spirit and scope of the invention.

What is claimed is:

1. An angioplasty catheter, comprising:
 a single element, longitudinally extending flexible shaft which has a proximal section and a distal section, the proximal section having an inflation lumen extending longitudinally therethrough and the distal section having a proximal transition portion and a distal core portion, with the transition portion having a distally decreasing outer diameter and the distal core portion having a solid cross section; and
 a balloon circumscribing the shaft which has a proximal segment, an intermediate inflatable segment, and a distal segment, the proximal segment being sealably connected to the shaft, the distal segment being sealably connected to the distal core portion of the distal section of the shaft and the intermediate segment beginning distally of the proximal transition portion of the distal section of the shaft and in fluid communication with the inflation lumen.

2. The angioplasty catheter of claim 1, and further comprising:
 a flexible tip extending from the distal core portion of the distal section of the shaft.

3. The angioplasty catheter of claim 2, wherein the flexible tip is mounted to the distal core portion adjacent the distal segment of the balloon.

4. The angioplasty catheter of claim 2, wherein the flexible tip is soldered to the distal core portion of the distal section of the shaft.

5. The angioplasty catheter of claim 2, wherein the flexible tip is a coil spring tip.

6. The angioplasty catheter of claim 5, wherein the single element shaft tapers at the transition portion to form a safety wire attached to an end cap of the coil spring tip.

7. The angioplasty catheter of claim 1, wherein the transition portion tapers uniformly from a proximal end of the transition portion to a distal end of the transition portion.

8. The angioplasty catheter of claim 1, wherein the shaft is formed from a stainless steel hypotube.

9. The angioplasty catheter of claim 1, wherein the shaft is coated with a lubricous material.

10. The angioplasty catheter of claim 1, wherein the shaft is formed from semi-rigid plastic tubing.

11. The angioplasty catheter of claim 10, wherein the transition portion of the distal section of the shaft tapers uniformly to the distal core portion and wherein the distal core portion of the distal section of the shaft is formed about a metal core wire.

12. The angioplasty catheter of claim 11, wherein a diameter of the metal core wire decreases distally to form a safety wire.

13. The angioplasty catheter of claim 1, wherein the shaft has at least one aperture through its transition portion to provide fluid communication between the inflation lumen and the intermediate inflatable segment of the balloon.

14. The angioplasty catheter of claim 1, wherein the balloon is formed from a polymeric material.

15. The angioplasty catheter of claim 1, wherein a radiopaque marker band circumscribes a portion of the shaft within the balloon.

16. The angioplasty catheter of claim 1, wherein the proximal and distal segments of the balloon are bonded to the shaft with epoxy.

17. The angioplasty catheter of claim 1, and further comprising:
a bond between the transition portion and the proximal segment of the balloon such that the outer diameter of the catheter remains generally uniform.

18. An angioplasty catheter, comprising:
a single element, longitudinally extending flexible shaft which has a proximal section and a distal section, the proximal section having an inflation lumen extending longitudinally therethrough and the distal section having a proximal transition portion and a distal core portion, with the transition portion having a distally decreasing outer diameter and the distal core portion having a solid cross section; and
a balloon circumscribing the shaft which has a proximal segment, an intermediate inflatable segment, and a distal segment, the proximal segment being sealably connected to the shaft, the distal segment being sealably connected to the distal core portion of the distal section of the shaft and the intermediate segment beginning distally of the proximal transition portion of the distal section of the shaft and in fluid communication with the inflation lumen.
a wire portion formed in the distal core portion of the distal section of the shaft with the wire portion being of reduced diameter from the distal core portion and extending distally thereof; and
a flexible coil spring mounted on the distal core portion of the distal section of the shaft to extend about the wire portion, with the coil spring secured to a distal end of the wire portion.

19. A method of manufacturing an angioplasty balloon catheter which comprises the steps of:
forming a single element shaft having an inflation lumen and a proximal section and a distal section;
forming a proximal part of the distal section of the shaft into a transition portion wherein the cross-sectional diameter of the shaft is reduced distally;
forming a distal part of the distal section into a generally solid distal core;
mounting an inflatable balloon on the distal section of the shaft, with a proximal segment of the balloon secured to the shaft, with a distal segment of the balloon secured to the generally solid distal core, and with an intermediate inflatable segment of the balloon beginning distally of the proximal transition portion of the distal section of the shaft; and
providing a means of fluid communication between the balloon and the inflation lumen.

20. The method of claim 19, and further comprising the steps of:
forming the solid distal core into a solid distal core wire; and
further reducing the cross-sectional diameter of the solid distal core wire to define a distal safety wire segment of the shaft.

21. The method of claim 20, and further comprising the step of:
securing a coil spring to the solid distal core wire to extend distally from the balloon about the distal safety wire segment.

22. The method of claim 21, and further comprising the step of:
securing a distal end of the distal safety wire segment to a distal end cap mounted on the coil spring.

23. The method of claim 19, and further comprising the step of:
uniformly decreasing the cross-sectional diameter of the transition portion of the shaft distally.

24. The method of claim 19, and further comprising the step of:
bonding the proximal segment of the balloon to the transition portion such that the overall diameter of the catheter remains generally uniform.

25. The method of claim 19, and further comprising the step of:
providing at least one aperture for fluid communication between the balloon and the inflation lumen.

26. A method of manufacturing an angioplasty balloon catheter which comprises the steps of:
forming a single element shaft having an inflation lumen and a proximal section and a distal section;
forming a proximal transition portion from the distal section of the shaft wherein the cross-sectional diameter of the shaft is reduced distally;
forming a distal core portion of the distal section of the shaft into a metal core wire;
mounting an inflatable balloon on the distal section of the shaft, with a proximal segment of the balloon secured to the shaft, a distal segment of the balloon secured to the distal core portion and an intermediate inflatable segment beginning distally of the proximal transition portion of the distal section of the shaft; and
providing a means of fluid communication between the intermediate inflatable segment of the balloon and the inflation lumen.

27. The method of claim 26, and further comprising the step of:
further reducing the cross-sectional diameter of the metal core wire to define a distal safety wire segment of the shaft.

28. The method of claim 27, and further comprising the step of:
securing a coil spring to the metal core wire to extend distally from the balloon about the distal safety wire segment.

29. The method of claim 28, and further comprising the step of:
securing a distal end of the distal safety wire segment to a distal end cap mounted on the coil spring.

30. The method of claim 26, and further comprising the step of:
uniformly decreasing the cross-sectional diameter of the transition portion of the shaft distally.

31. The method of claim 26, and further comprising the step of:

bonding the proximal segment of the balloon to the transition portion such that the overall diameter of the catheter remains generally uniform.

32. The method of claim 26, and further comprising the step of:
providing at least one aperture for fluid communication between the intermediate inflatable segment and the inflation lumen.

33. An angioplasty catheter, comprising:
a longitudinal extending flexible shaft which has a proximal section and a distal section, the proximal section having an inflation lumen extending longitudinally therethrough and the distal section comprising a single element having a proximal transition portion and a distal core portion, with the transition portion providing a distally decreasing shaft outer diameter and the distal core portion having a solid cross section; and
a balloon circumscribing the shaft having a proximal segment, an intermediate inflatable segment, and a distal segment, the proximal segment being sealably connected to the shaft, the distal segment being sealably connected to the distal core portion of the distal section of the shaft and the intermediate segment being in fluid communication with the inflation lumen.

34. The angioplasty catheter of claim 23, wherein the intermediate inflatable segment of the balloon is distal of the proximal transition portion of the distal section of the shaft.

35. The angioplasty catheter of claim 23 wherein the proximal transition portion includes at least one aperture through a side wall thereof to provide fluid communication between the inflation lumen and the intermediate inflatable segment of the balloon.

36. The angioplasty catheter of claim 33 and further comprising:
a flexible tip extending from the distal core portion of the distal section of the shaft.

37. The angioplasty catheter of claim 36 wherein the flexible tip is mounted to the distal core portion adjacent the distal segment of the balloon.

38. The angioplasty catheter of claim 36 wherein the flexible tip is soldered to the distal core portion of the distal section of the shaft.

39. The angioplasty catheter of claim 36 wherein the flexible tip is a coil spring tip.

40. The angioplasty catheter of claim 39 including a safety wire extending from the distal core portion of the shaft and attached to an end cap of the coil spring tip.

41. The angioplasty catheter of claim 33 wherein the transition portion tapers uniformly from a proximal end of the transition portion to a distal end of the transition portion.

42. The angioplasty catheter of claim 33 wherein the shaft is form from a stainless steel hypotube.

43. The angioplasty catheter of claim 33 wherein the shaft is coated with a lubricous material.

44. The angioplasty catheter of claim 33 wherein the shaft is formed from semi-rigid plastic tubing.

45. The angioplasty catheter of claim 44 wherein the transition portion of the distal section of the shaft tapers uniformly to the distal core portion and wherein the distal core portion of the distal section of the shaft is formed about a metal core wire.

46. The angioplasty catheter of claim 45 wherein a diameter of the metal core wire decreases distally to form a safety wire.

47. The angioplasty catheter of claim 33 wherein the proximal and distal segments of the balloon are bonded to the shaft with an epoxy.

48. The angioplasty catheter of claim 33 wherein the proximal segment of the balloon is formed of a flexible plastic tube having a proximal end sealably connected to the shaft and a distal end sealably connected to a proximal end of the inflatable balloon segment.

49. The angioplasty catheter wherein an elongated shaft supports an inflatable balloon at a distal end thereof, the improvement comprising:
a shaft including a proximal section having an inflation lumen therethrough, the inflation lumen being in fluid communication with an interior of the balloon, and a distal section, the distal section comprising a single element having a proximal transition portion and a distal core portion extending through the interior of the balloon, with the transition portion providing a distally decreasing shaft outer diameter and the distal core portion having a solid cross section terminating the inflation lumen.

* * * * *

UNITED STATES PATENT AND TRADEMARK OFFICE
CERTIFICATE OF CORRECTION

PATENT NO. : 5,156,595

DATED : October 20, 1992

INVENTOR(S) : DANIEL O. ADAMS

It is certified that error appears in the above-identified patent and that said Letters Patent is hereby corrected as shown below:

Col. 9, line 27, delete "claim 23", insert "claim 33"

Col. 9, line 31, delete "claim 23", insert "claim 33"

Col. 10, line 32, delete "The", insert "In an"

Signed and Sealed this

Twenty-first Day of December, 1993

Attest:

BRUCE LEHMAN

Attesting Officer  Commissioner of Patents and Trademarks